US007619123B2

(12) United States Patent
Ji et al.

(10) Patent No.: US 7,619,123 B2
(45) Date of Patent: Nov. 17, 2009

(54) METHODS FOR STABILIZING LITHIATED HALOGEN-SUBSTITUTED AROMATIC COMPOUNDS

(75) Inventors: Yaohui Ji, Florence, SC (US); Thimma Rawalpally, Florence, SC (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 12/257,419

(22) Filed: Oct. 24, 2008

(65) Prior Publication Data

US 2009/0118546 A1 May 7, 2009

Related U.S. Application Data

(60) Provisional application No. 60/984,779, filed on Nov. 2, 2007.

(51) Int. Cl.
*C07C 45/00* (2006.01)
(52) U.S. Cl. ...................................... 568/426; 568/437
(58) Field of Classification Search ................. 568/426, 568/437
See application file for complete search history.

(56) References Cited

FOREIGN PATENT DOCUMENTS

WO   WO 2004/099164   11/2004

OTHER PUBLICATIONS

Cantrell, A et al *Jour. of Med. Chem.* 39(21), 4261-4274 (1996).
Adejare, A. et al *Tetrahedron Ltrs*, 25(49), 5597-5598 (1984).
Hacan A et al *Tetrahedron Ltrs* 45(36), 6697-6702, (2004).
Rawalpally, T et al *Organic Process Res and Dev*, 12(6), 1293-1298, (2008).
Fotouhi et al., J. Med. Chem. vol. 49, pp. 6549-6560 (2006).
Boot, et al., Bioorganic & Medicinal Chemistry Letters, vol. 14 pp. 5395-5399 (2004).
Rodney, L. P., Current Opinion in Drug Discovery & Development vol. 3(6) pp. 783-792 (2000).
Fernandez, P., Organic Process Research & Development, vol. 9 pp. 764-767 (2005).
Schwartz E., Tetrahedron Letters, vol. 33(49) pp. 7499-7502 (1992).
Kirk, L. K., J. Org. Chem. vol. 53, pp. 3145-3147 (1988).
Ladd et al., J. Org. Chem. vol. 46 pp. 203-206 (1981).
Kirk, L. K. J. Org. Chem. vol. 51 pp. 4073-4075 (1986).
Ansel, Pharmaceutical Dosage Forms & Drug Delivery Systems pp. 456-457 (1995).

*Primary Examiner*—Sikarl A Witherspoon
(74) *Attorney, Agent, or Firm*—George W. Johnston; Patricia S. Rocha-Tramaloni; Kimberly J. Prior

(57) ABSTRACT

The present invention provides novel methods for stabilizing lithiated halogen-substituted aromatic compounds. In particular, the method is useful for the preparation of 2-methoxy-5,6-difluorobenzaldehyde, an important intermediate for the preparation of [4-amino-2-(1-methanesulfonylpiperidin-4-ylamino)pyrimidin-5-yl](2,3-difluoro-6methoxyphenyl)methanone, a potent and selective inhibitor of CDK4/Cyclin D1, CDK2/Cyclin E and CDK1/Cyclin B. The method is also useful for stabilizing other lithiated halogen-substituted aromatic compounds and is particularly useful for scale up reactions where the exothermic nature of the reaction can lead to reaction runway.

18 Claims, 5 Drawing Sheets

Reaction profile of Lithiated 3, 4-difluoroanisole

Reaction Profile of Lithiated 3, 4-difluoroanisole (0.471 mol/liter) (Dilute Solution)

Reaction Profile of lithiated 3, 4-difluoroanisole with MgCl$_2$

Reaction profile of Lithiated 3-bromochlorobenzene with MgCl$_2$

Reaction profile of lithiated 3-bromochlorobenzene without MgCl$_2$

METHODS FOR STABILIZING LITHIATED HALOGEN-SUBSTITUTED AROMATIC COMPOUNDS

PRIORITY TO RELATED APPLICATIONS

This application claims the benefit of U.S. Provisional Application No. 60/984,779, filed Nov. 2, 2007, which is hereby incorporated by reference in its entirety.

FIELD OF THE INVENTION

The present invention provides novel methods for stabilizing lithiated halogen-substituted aromatic compounds. In particular, the method is useful for the preparation of 2-methoxy-5,6-difluorobenzaldehyde, an important intermediate for the preparation of [4-amino-2-(1-methanesulfonylpiperidin-4-ylamino) pyrimidin-5-yl](2,3-difluoro-6methoxyphenyl) methanone, a potent and selective inhibitor of CDK4/Cyclin D1, CDK2/Cyclin E and CDK1/Cyclin B. The method is also useful for stabilizing other lithiated halogen-substituted aromatic compounds and is particularly useful for scale up reactions where the exothermic nature of the reaction can lead to reaction runway.

BACKGROUND OF THE INVENTION

The disclosures referred to herein to illustrate the background of the invention and to provide additional detail with respect to its practice are incorporated herein by reference and, for convenience, are referenced in the following text and respectively grouped in the appended bibliography.

Normal cell proliferation is regulated to a large degree by cyclin-dependent kinases (CDKs), which control cell cycle transitions through growth phases associated with DNA replication (S) and mitosis (M). Tumor cells exhibit mutations and can alter control mechanisms for passage through these transition points by a variety of mechanisms associated with the loss of normal cyclin-dependent kinase (CDK) activity. Evidence indicates that restoring CDK activity to normal catalytic activity levels can prevent tumor growth. The cyclin-dependent kinases play a critical role in cell cycle regulation. The sequential control of the various CDKs by cyclins allows for the proper progression through the cell cycle. In some tumors, increased levels of CDK proteins and cyclins are often found. Inhibitors of CDK may therefore be effective modulators of cell proliferation. Compound (1) ([4-amino-2-(1-methanesulfonylpiperidin-4-ylamino) pyrimidin-5-yl](2,3-difluoro-6methoxyphenyl)methanone) is known to be a potent and selective inhibitor of CDK4/Cyclin D1, CDK2/Cyclin E, and CDK1/Cyclin B.

Currently, there are no safe and effective marketed agents that act primarily to inhibit CDK or Cyclins. The sulfonate salt (primary amine) of compound (1) is currently being developed as an intravenous agent to inhibit CDK1. The method for preparing compound (1) and its use for the treatment for solid tumors are known[1]. Compound (1) can be prepared via dichloro-pyrimidine intermediate (4) which in turn is prepared by coupling 2-methoxy-5,6-difluorobenzaldehyde (2) and 5-bromo-2,4-dichloro-pyrimidine (3) as set out in Scheme 1.

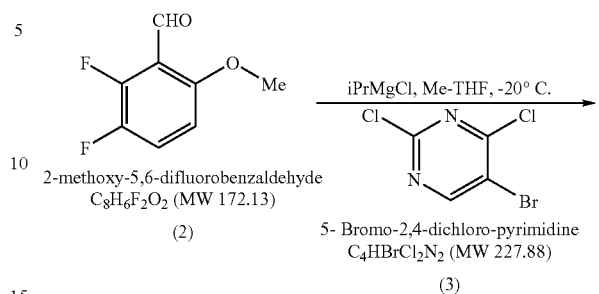

Scheme 1

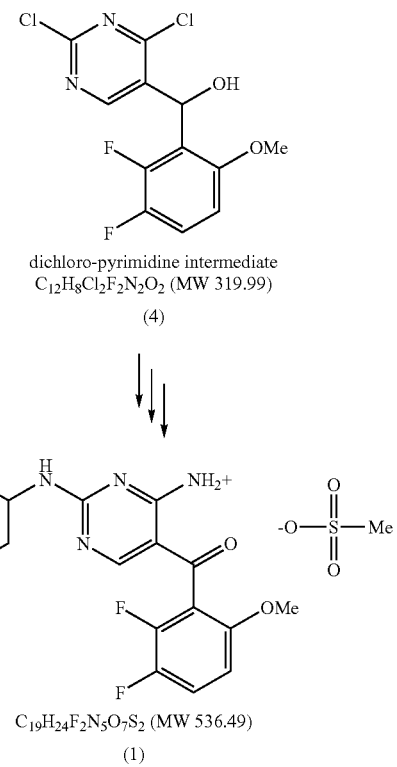

2-Methoxy-5,6-difluorobenzaldehyde (2) is a key intermediate for the synthesis of compound (1) and other drug candidates. The synthetic route for preparing intermediate (2) has been disclosed[2] and involves a low temperature (−78° C.) metalation/formylation of 3,4-difluoroanisole (5) as set out in Scheme 2.

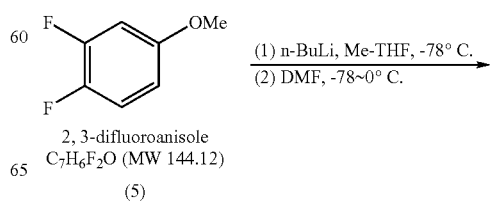

Scheme 2

-continued

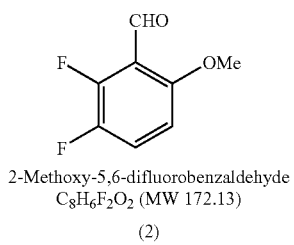

2-Methoxy-5,6-difluorobenzaldehyde
C$_8$H$_6$F$_2$O$_2$ (MW 172.13)

(2)

The low temperature ortho-lithiation of halo-substituted aromatics method has safety issues because of the formation of the highly energetic and unstable benzyne intermediate[3]. On scale up, the rate of formation of this unstable intermediate increases substantially due to loss of cooling which can lead to a reaction runway, which may result in equipment damage and loss of containment. An uncontrolled charge of n-BuLi can also lead to a reaction runway. The benzyne intermediate anion[3] in the halo-substituted aromatic reactions is known to be thermally unstable.

Accordingly, novel methods for stabilizing the reactions of low temperature lithiation of halogen-substituted aromatic compounds are required.

SUMMARY OF THE INVENTION

The present invention provides a method for preparing compound (2) from compound (5) having the formula:

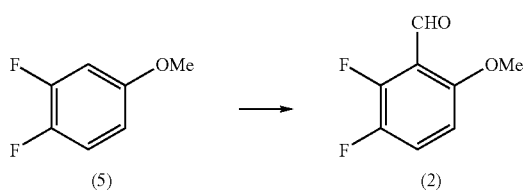

which comprises:

(a) admixing 3,4-difluoroanisole (5) with anhydrous magnesium chloride in an inert organic solvent;

(b) cooling the admixture from step (a) to about −78° C.;

(c) adding n-BuLi to the admixture in step (b) maintaining the temperature at about <−75° C.;

(d) adding N,N-dimethylformamide to the admixture in step (c) at about −78° C. maintaining the temperature at about <−75° C.;

(e) warming the admixture in step (d) to about 0° C. and then quenching the admixture with an aqueous acidic solution; and (f) separating the organic solution from the aqueous solution in step (e) to provide compound (2) in the organic solution.

The present invention also provides a method for preparing compound (12) from compound (10) having the formula:

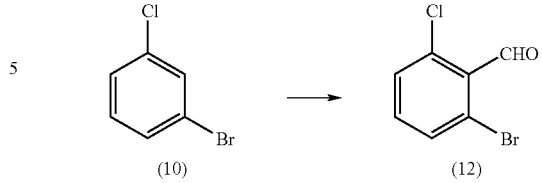

which comprises:

(a) admixing 3-bromochlorobenzene (10) with anhydrous magnesium chloride in an inert organic solvent;

(b) cooling the admixture from step (a) to about −78° C.;

(c) adding lithium diisopropylamide to the admixture in step (b) maintaining the temperature at about <−75° C.;

(d) adding N,N-dimethylformamide to the admixture in step (c) at about −78° C. maintaining the temperature at about <−75° C.;

(e) warming the admixture in step (d) to about 0° C. and then quenching the admixture with an aqueous acidic solution; and (f) separating the organic solution from the aqueous solution in step (e) to provide compound (12) in the organic solution.

DETAILED DESCRIPTION OF THE INVENTION

Figure 1:
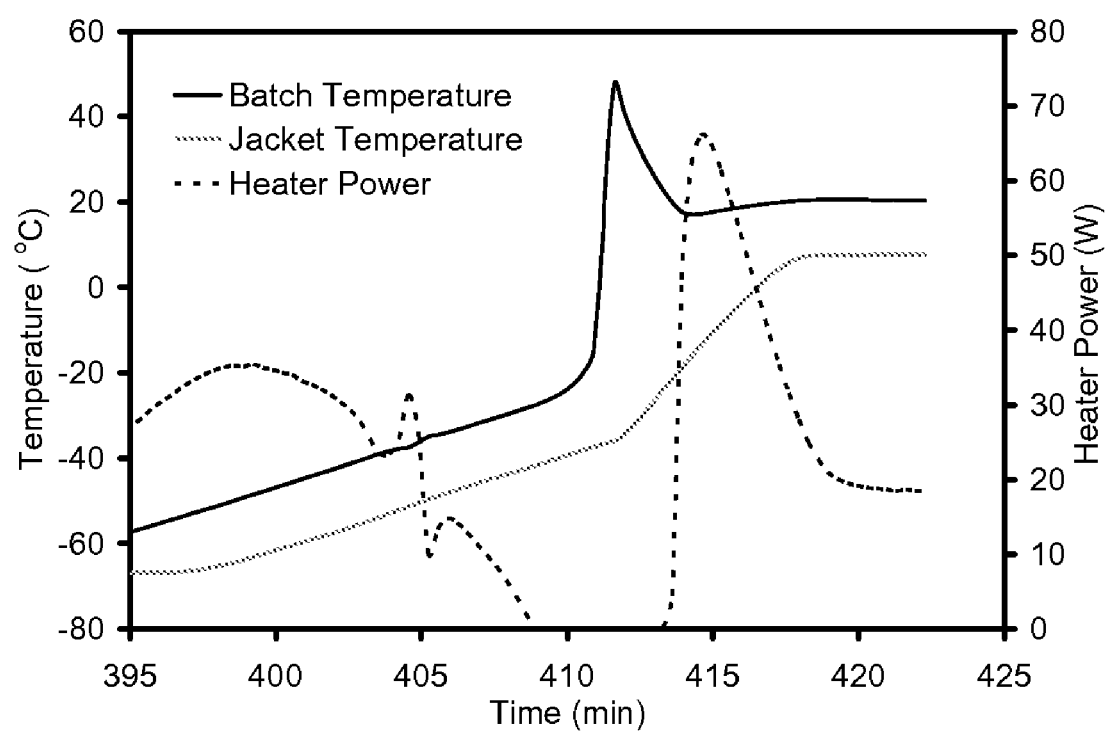
FIG. 1 is a diagram illustrating the reaction profile of lithiated 3,4-difluoroanisole.

The present invention provides novel methods for stabilizing lithiated halogen-substituted aromatic compounds. The method is particularly useful for scale up reactions where the exothermic nature of the reaction can lead to reaction runway.

As used herein, the following terms have the meanings set out below.

The term "halogen" refers to chloro, bromo, iodo and fluoro, and is preferably chloro.

The term "inert organic solvent" refers to a solvent that does not interfere chemically with the reaction.

The term "pharmaceutically acceptable," such as pharmaceutically acceptable carrier, excipient, etc., means pharmacologically acceptable and substantially non-toxic to the subject to which the particular compound is administered.

The term "pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium, and quaternary ammonium hydroxides, such as for example, tetramethylammonium hydroxide. Chemical modification of a pharmaceutical compound (i.e., drug) into a salt is a technique well known to pharmaceutical chemists to obtain improved physical and chemical stability, hydroscopicity, and solubility of compounds. See, e.g., H. Ansel et. al., Pharmaceutical Dosage Forms and Drug Delivery Systems (6$^{th}$ Ed. 1995) at pp. 196 and 1456-1457.

The term "prodrug" refers to compounds, which undergo transformation prior to exhibiting their pharmacological effects. The chemical modification of drugs to overcome pharmaceutical problems has also been termed "drug latentiation." Drug latentiation is the chemical modification of a biologically active compound to form a new compound, which upon in vivo enzymatic attack will liberate the parent compound. The chemical alterations of the parent compound are such that the change in physicochemical properties will affect the absorption, distribution and enzymatic metabolism. The definition of drug latentiation has also been extended to include nonenzymatic regeneration of the parent compound. Regeneration takes place as a consequence of hydrolytic, dissociative, and other reactions not necessarily enzyme mediated. The terms prodrugs, latentiated drugs, and bio-reversible derivatives are used interchangeably. By inference, latentiation implies a time lag element or time component involved in regenerating the bioactive parent molecule in vivo. The term prodrug is general in that it includes latentiated drug derivatives as well as those substances, which are converted after administration to the actual substance, which combines with receptors. The term prodrug is a generic term for agents, which undergo biotransformation prior to exhibiting their pharmacological actions.

In one embodiment, the present invention provides a method for preparing compound (2) from compound (5) having the formula:

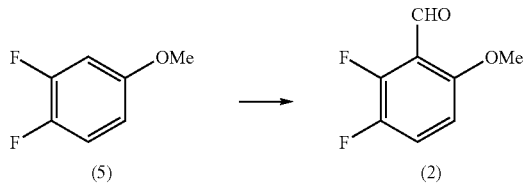

which comprises (a) admixing 3,4-difluoroanisole (5) with anhydrous magnesium chloride in an inert organic solvent; (b) cooling the admixture from step (a) to about −78° C.; (c) adding n-BuLi to the admixture in step (b) maintaining the temperature at about <−75° C.; (d) adding N,N-dimethylformamide to the admixture in step (c) at about −78° C. maintaining the temperature at about <−75° C.; (e) warming the admixture in step (d) to about 0° C. and then quenching the admixture with an aqueous acidic solution; and (f) separating the organic solution from the aqueous solution in step (e) to provide compound (2) in the organic solution.

Preferably, the inert organic solvent in step (a) is selected from the group consisting of 2-methyltetrahydrofuran, tetrahydrofuran, and diethyl ether. More preferably, the inert organic solvent is 2-methyltetrahydrofuran.

Preferably, the molar ratio of (5) to magnesium chloride in step (a) is about 1:1.1, respectively. Preferably, the n-BuLi in step (c) is a 2.5M solution in hexanes. Preferably, the molar ratio of n-BuLi to (5) in step (c) is about 1.3:1, respectively.

Preferably, the molar ratio of N,N-dimethylformamide to (5) in step (d) is about 1.4:1, respectively.

Preferably, the aqueous acidic solution in step (e) is selected from the group consisting of citric acid solution, acetic acid, and formic acid. More preferably, the aqueous acidic solution is a citric acid solution.

In another embodiment, the present invention provides a method for preparing compound (12) from compound (10) having the formula:

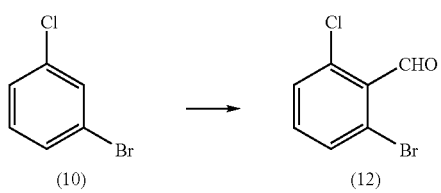

which comprises (a) admixing 3-bromochlorobenzene (10) with anhydrous magnesium chloride in an inert organic solvent; (b) cooling the admixture from step (a) to about −78° C.; (c) adding lithium diisopropylamide to the admixture in step (b) maintaining the temperature at about <−75° C.; (d) adding N,N-dimethylformamide to the admixture in step (c) at about −78° C. maintaining the temperature at about <−75° C.; (e) warming the admixture in step (d) to about 0° C. and then quenching the admixture with an aqueous acidic solution; and (f) separating the organic solution from the aqueous solution in step (e) to provide compound (12) in the organic solution.

Preferably, the inert organic solvent in step (a) is selected from the group consisting of 2-methyltetrahydrofuran, tetrahydrofuran, and diethyl ether. More preferably, the inert organic solvent is 2-methyltetrahydrofuran.

Preferably, the molar ratio of (10) to magnesium chloride in step (a) is about 1:1.1, respectively. Preferably, the lithium diisopropylamide in step (c) is a 2M solution in heptane/tetrahydrofuran. Preferably, the molar ratio of lithium diisopropylamide to (10) in step (c) is about 1.3:1, respectively. Preferably, the molar ratio of N,N-dimethylformamide to (10) in step (d) is about 1.4:1, respectively.

Preferably, the aqueous acidic solution in step (e) is selected from the group consisting of citric acid solution, acetic acid, and formic acid. More preferably, wherein the aqueous acidic solution is a citric acid solution.

Because the low temperature ortho-lithiation of halo-substituted aromatics method has exothermic safety issues, an initial approach was to determine the thermal stability of the 3,4-difluoroanisole anion (6).

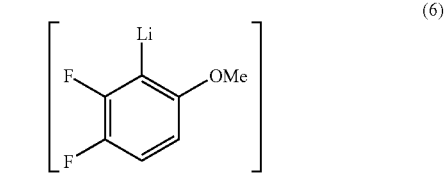

Lithiated-2,3-difluoroanisole intermediate

The thermal characteristics of this reaction were studied using an HEL Simular reaction calorimeter (a reaction calorimeter that allows for the simulation and thermal study of a plant level chemistry reaction). The calorimeter is equipped with a double-jacketed, 0.8-liter, glass reactor (6 bar). The inner jacket contains a heat-transfer fluid and the outer jacket is evacuated to insulate the system. The lithiated anion (6) was generated by the addition of 2.5 M n-BuLi in hexanes (1.3 equivalents) to a 2-methyltetrahydrofuran solution containing 3,4-difluoroanisole (5) (final concentration 0.864 gmol/liter) while maintaining a batch temperature of less than −60° C. The calorimeter was operated in power compensation mode, which maintains the jacket at a fixed temperature below the batch temperature setpoint (in this study, 12° C. below the setpoint) and uses a coil heater inserted into the batch to compensate for the heat removed by the jacket and to maintain the batch temperature setpoint. After the n-BuLi addition was complete, the batch was heated at 2° C./min. A maximum power-input in the power compensation mode was measured at a batch temperature of −50° C. The power-input needed to heat the batch declined steadily when the release of energy via decomposition of the reaction mass increased. The batch went into run-away mode at −30° C. (jacket −42° C.) and the batch temperature increased at an accelerating rate with a peak temperature of 50° C. The maximum self-heating rate (dT/dt) observed was 120° C./min (jacket at −40° C.) and the maximum deviation from setpoint was 70° C. The energy release potential and adiabatic temperature rise were calculated by estimating the cp (specific heat capacity at constant pressure) of the reactor contents to be at 1.85 J/(g. ° C.) and taking an average of pre-and post-decomposition power compensation readings and are set out in FIG. 1.

Based on literature precedence, the halo-substituted lithiated anion (6) was postulated to decompose via the highly energetic benzyne intermediate (7) as set out in Scheme 3.

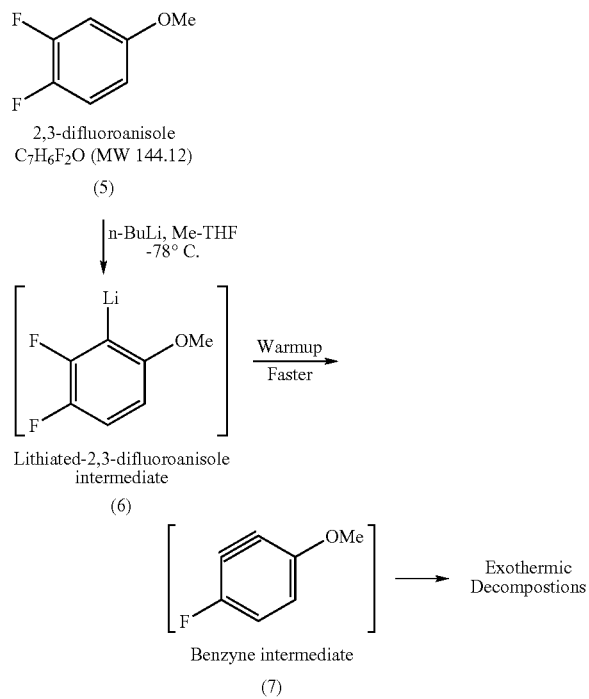

Scheme 3

Figure 2:
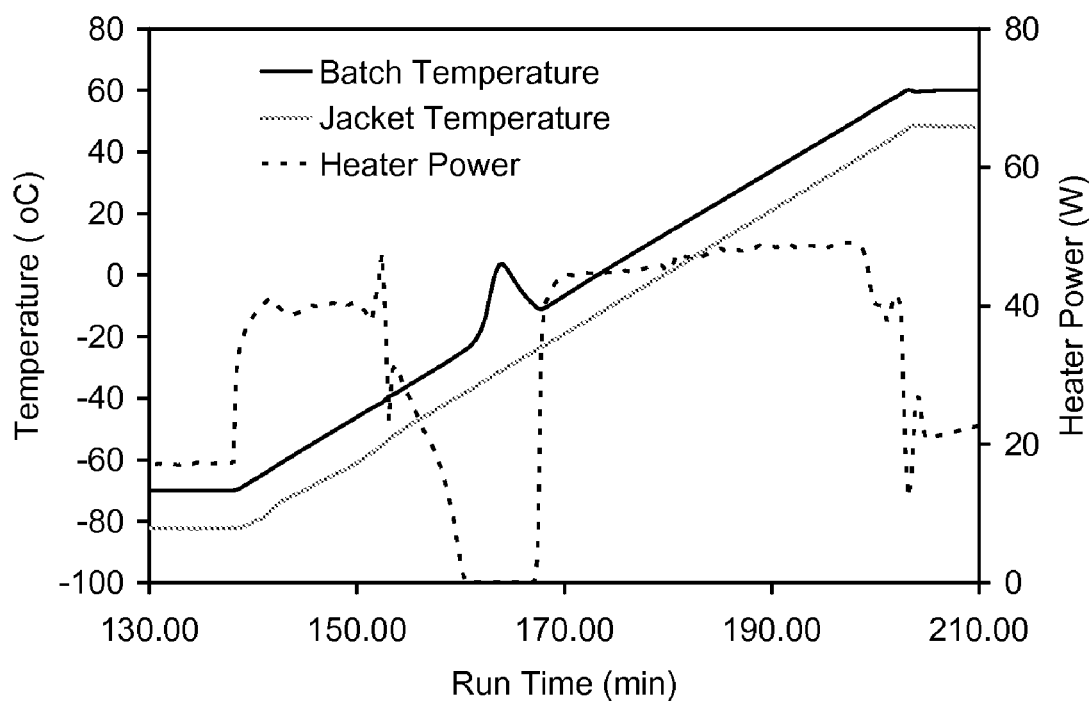
FIG. 2 is a diagram illustrating the reaction profile of lithiated 3,4-difluoroanisole (0.471 mol/liter).

To avoid the thermal instability of the lithiated intermediate (6) in the ortho-lithiation method, alternate reaction methods were explored but none were successful. Another option was to carry out the lithiated halogen-substituted aromatic compound reaction in a dilute solution (0.471 gmol/liter). A second HEL reaction calorimeter experiment was therefore run doubling the original amount of 2-methyltetrahydrofuran. After lithiation below −70° C., the batch was heated at 2° C./min to a final temperature of 40° C. Again, an exotherm was noted beginning at about −43° C. and the batch temperature continued to increase until it reached a maximum of 21° C. from its set point. The increased heat capacity of the system (dilute reaction) absorbed the heat better thereby minimizing benzyne (7) formation. Decomposition still occurred under the dilute reaction conditions but the reaction-runaway was not observed (FIG. 2). Although diluting the reaction provides some solution, it reduces the reaction capacity and increases waste disposal costs due to the increase in solvent used.

Figure 3:
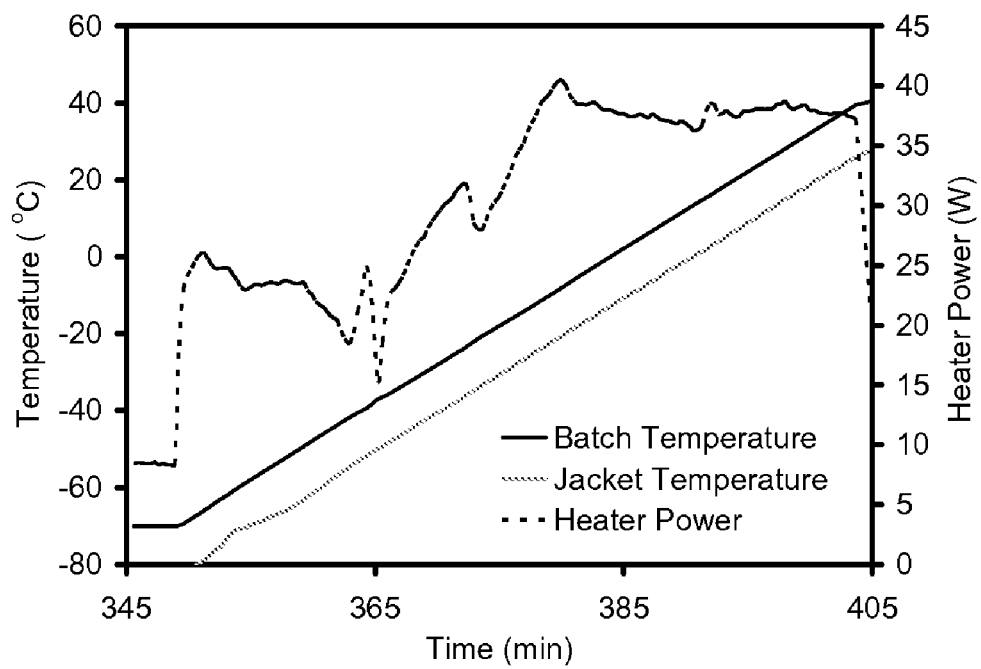
FIG. 3 is a diagram illustrating the reaction profile of lithiated 3,4-difluoroanisole with MgCl$_2$.

The present invention provides a safer scale up method for preparing the key intermediate 2-methoxy-5,6-difluorobenzaldehyde (2). The reaction runaway hazard can be eliminated by using anhydrous $MgCl_2$ as an additive to complex with and stabilize the reactive species and slow down the rate of decomposition. The phenomenon was initially observed and studied with 3,4-difluoroanisole (5) as a substrate and was also successfully extended to other halo-substituted aromatic compounds. While not wishing to be bound by theory, applicants have conducted thermochemical experiments, which suggest that $MgCl_2$ acts by forming a weak interaction with the lithiated species, rather than by a complete exchange with the Li ion. This process was successfully piloted on a large scale in the presence of the anhydrous $MgCl_2$ additive. The standard procedure involves adding anhydrous magnesium chloride to a solution of 3,4-difluoroanisole (5) in 2-methyltetrahydrofuran and stirring the slurry for 15-20 hours. The slurry is then cooled to −78° C. and n-BuLi (1.3 equivalents) is admixed into the reaction mixture. Under these conditions, the lithiated 3,4-difluoroanisole anion (6), when heated with a steady ramp of 2° C./min from −70° C. to 40° C., did not cause a run-away reaction (FIG. 3).

A local maximum in the power-comp heater was seen at −49° C., but the rate of decomposition is not sufficient to cause a runaway unlike the case without anhydrous $MgCl_2$. At all times during the heating phase power input into the reactor was greater than either of the baselines resulting in a system that was more conservative than adiabatic.

An additional advantage in using anhydrous $MgCl_2$ in the reaction results in higher quality of compound (2) (white color as opposed to an earlier light-yellow to yellow color). The colored impurity is an issue in the downstream process. The higher purity profile of compound (2) in presence of anhydrous $MgCl_2$ can be attributed to fewer side reactions due to stabilization of the lithiated intermediate (6).

Figure 4:
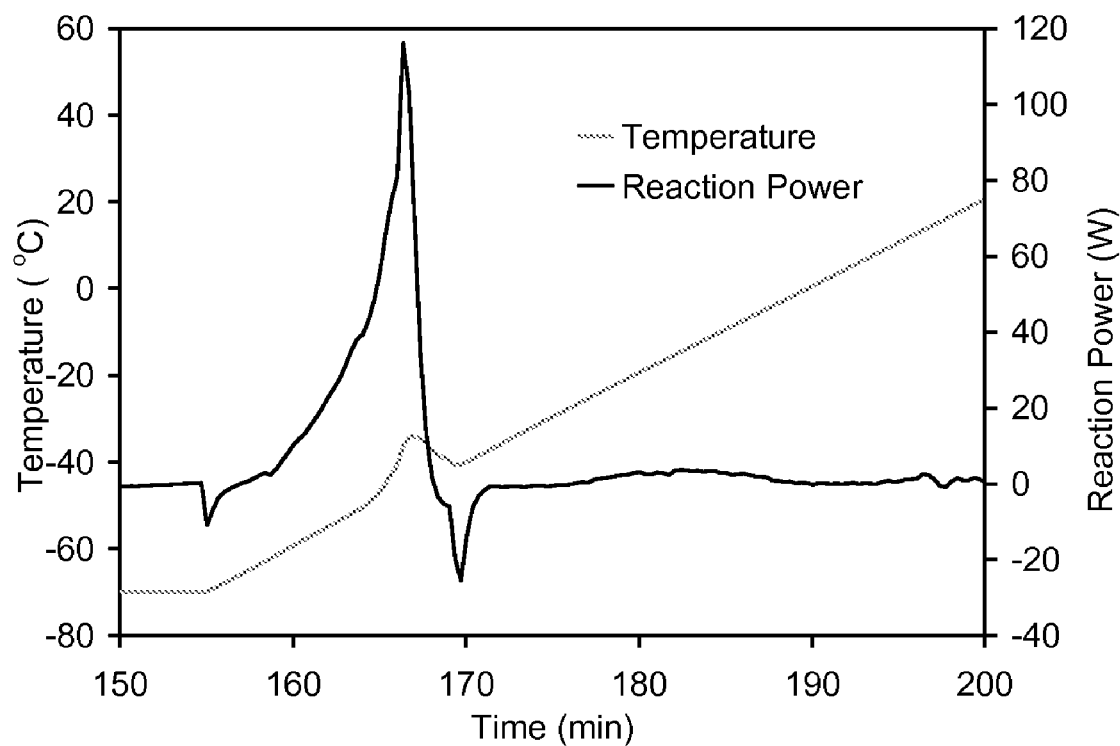
FIG. 4 is a diagram illustrating the reaction profile of lithiated 3-bromochlorobenzene with MgCl$_2$.
Figure 5:
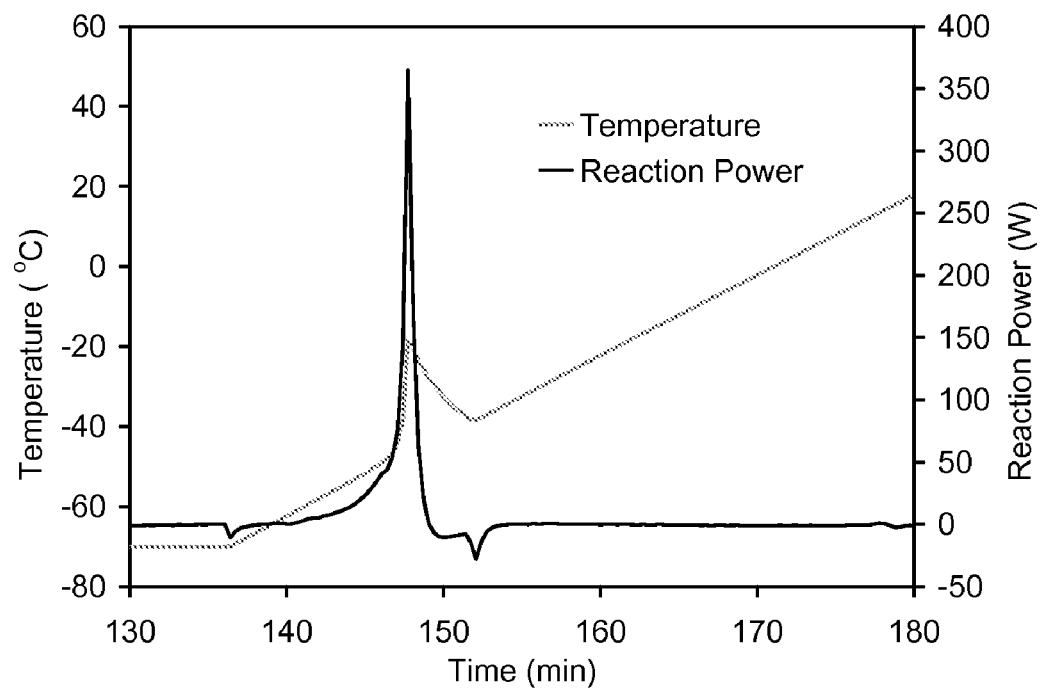
FIG. 5 is a diagram illustrating the reaction profile of lithiated 3-bromochlorobenzene without MgCl$_2$.

Similarly, the lithiated 3-bromochlorobenzene intermediate (11)[3b] showed a relatively mild exotherm in the presence of magnesium chloride upon warming (FIG. 4). A higher exotherm was observed when the lithiated 3-bromochlorobenzene intermediate (11) was warmed in the absence of anhydrous $MgCl_2$ (FIG. 5).

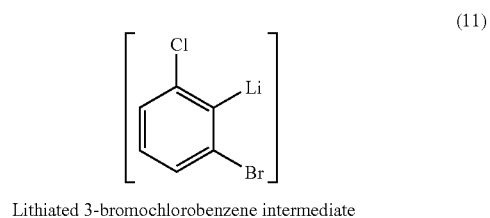

(11)

Lithiated 3-bromochlorobenzene intermediate

Additional details regarding the effect of anhydrous MgCl$_2$ on the thermal hazards presented by lithiated halogen-substituted aromatic compounds are set out in Table 1.

TABLE 1

Evaluation of MgCl$_2$ in halogen substituted aromatic compounds

| Substrate | Concentration (gmol/liter) | Adiabatic Temp. Rise (° C.) | (dT/dt)$_{max}$ (° C./min) | ΔH$_{rxn}$ (kJ/gmol) |
|---|---|---|---|---|
| F-, F, OMe (3,4-difluoroanisole) | 0.864 | 102 | 120 | −199 |
| F-, F, OMe + MgCl$_2$ | 0.864 | NA | 2 C./min | −199 |
| Cl, Br (3-bromochlorobenzene) | 0.488 | 49 | 52 | −151 |
| Cl, Br + MgCl$_2$ | 0.488 | 45 | 15 | −144 |

The compounds of the present invention can be prepared according to the examples set out below. The examples are presented for purposes of demonstrating, but not limiting, the preparation of the compounds and compositions of this invention.

EXAMPLES

In accordance with the present invention, the following examples are provided to illustrate the stabilization of lithiated halogen-substituted aromatic compounds in presence of MgCl$_2$.

Example 1

Preparation of 2-Methoxy-5,6-difluorobenzaldehyde (2) Starting from 3,4-Difluoroanisole (5)

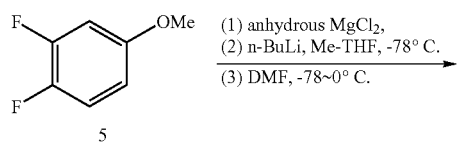

(1) anhydrous MgCl$_2$,
(2) n-BuLi, Me-THF, -78° C.
(3) DMF, -78~0° C.

-continued

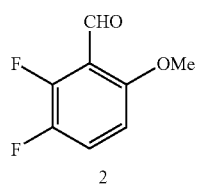

2

The thermal characteristics of this reaction were studied using an HEL Simular reaction calorimeter. The calorimeter was equipped with a double-jacketed, 0.8-liter, glass reactor (6 bar). The inner jacket contained a heat-transfer fluid and the outer jacket was evacuated to insulate the system. A quantity of 20.0 g (0.139 moles, 1 equivalent) of 3,4-difluoroanisole (5), 100 ml of 2-methyltetrahydrofuran (Me-THF) and 15.0 g (0.158 moles, 1.1 equivalents) of anhydrous magnesium chloride was charged to this reactor. The slurry was stirred for 20 hrs and then cooled to −78° C. A quantity of n-BuLi (2.5M in hexanes) 71.7 ml (0.179 moles, 1.3 equivalents) was charged into the batch, keeping the temp <−75° C. The batch was held for an hour and then 15.0 ml (0.194 moles, 1.4 equivalents) of N,N-dimethylformamide was added at −78° C., keeping the temperature <−75° C. The mixture was stirred for an hour and gradually warmed to 0° C. At 0° C., the reaction was quenched with 150 ml of 0.5M citric acid solution. The layers were separated and the organic layer was

Example 2

Preparation of 2-Bromo-6-chlorobenzaldehyde (12) Starting from 3-Bromochlorobenzene (10)

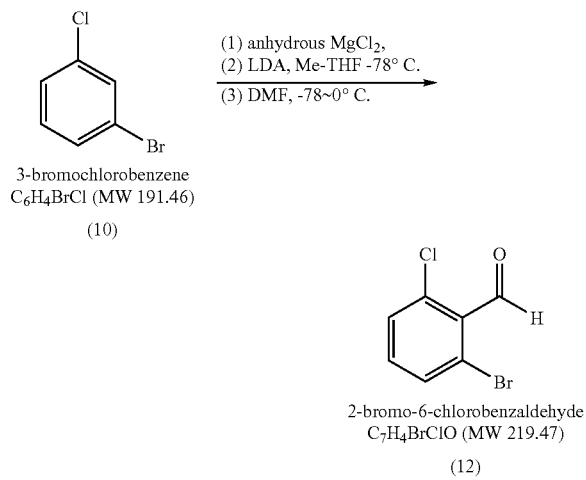

3-bromochlorobenzene
C₆H₄BrCl (MW 191.46)
(10)

(1) anhydrous MgCl$_2$,
(2) LDA, Me-THF -78° C.
(3) DMF, -78~0° C.

2-bromo-6-chlorobenzaldehyde
C₇H₄BrClO (MW 219.47)
(12)

The thermal characteristics of this reaction were studied using an HEL Simular reaction calorimeter. The calorimeter was equipped with a double-jacketed, 0.8-liter, glass reactor (6 bars). The inner jacket contained a heat-transfer fluid and the outer jacket was evacuated to insulate the system. A quantity of 26.5 g (0.139 moles, 1 equivalent) of 3-bromochlorobenzene (10), 200 ml of 2-methyltetrahydrofuran (Me-THF) and 15.0 g (0.158 moles, 1.1 equivalents) of anhydrous magnesium chloride was charged to this reactor. The slurry was then cooled to −78° C. A quantity of 91.2 ml (0.158 moles, 1.3 equivalents) of lithium diisopropylamide (LDA, 2M in heptane/THF) was charged into the batch, keeping the temp <−75° C. The batch was held for an hour after LDA addition. A quantity of 15.0 ml (0.194 moles, 1.4 equivalents) of N,N-dimethylformamide was charged into the batch at −78° C., keeping the temperature <−75° C. The mixture was stirred for an hour and gradually warmed to 0° C. At 0° C., the reaction was quenched with 150 ml of 0.5M citric acid solution. The layers were separated and the organic layer was collected and concentrated to dryness. The desired product (12) was isolated in 80% yield and 99% purity by GC.

REFERENCES (1) "Adventures in the Discovery and Development of a Novel CDK Inhibitor" (Green Corner report #1019905 by A. Lovey, presented at North Jersey ASC Organic Topical Group Fall Symposium, Oct. 21, 2005); "2,4-Diamino-5-ketopyrimidine: Synthesis and Structure-Activity Relationship of a Series of Novel and Potent CDK Inhibitors" by David Bartkovitz et al. at Fall 2005 ACS National Meeting, Washington, DC; Yi Ren's made a presentation at "Roche Excellence in Chemistry Symposium" in May 2006 at Palo Alto, and Chu, Xin-Jie; DePinto, W.; Bartkovitz, D.; So, Sung-Sau.; Vu, T.; Packman, K.; Lukacs, C.; Ding, Q.; Jiang, N.; Wang, K.; Goelzer, P.; Yin, X.; Smith, A. M.; Higgins, B. X.; Chen, Y.; Xiang, Q.; Moliterni, J.; Kaplan, G.; Graves, B.; Lovey, A.; Fotouhi, N. *J. Med. Chem.* 2006, 49, 6549-6560.

(2) Boot, J. R.; Brace, G.; Delatour, C. L.; Dezutter, N.; Fairhurst, J.; Findlay, J.; Gallagher, P. T.; Hoes, I.; Mahadevan, S.; Mitchell, S. N.; Rathmell, R. E.; Richards, S. J.; Simmonds, R. G.; Wallace, L.; Whatton. *Bioranganic & Medicinal Chemistry Letters.* 2004, 14, 5395-5399.

(3) (a) For example in Difluoro series: Rodney, L. P. Jr.; *Current Opinion in Drug Discovery & Development.* 2000, 3(6), 783-792. (b) Chlorobromophenyllithium: Hickey, R. M.; Allwein, P. S.; Nelson, D. T.; Kress, H. K.; Sudah, S. O.; Moment, J. A.; Rodgers, D, S.; Kaba, M.; Fernandez, P. *Organic Process Research & Development.* 2005, 9, 764-767. (c) 2,6-dibromophenyllithium: Lulinski, S.; Serwatowski, J. *J. Org. Chem.* 2003, 68, 5384. (d) Fluorine as an ortho-directing Group: Bridges, J. A.; Lee, A.; Maduakor, C. E.; Schwartz, E. *Tetrahedron Letters,* 1992, 33(49), 7499-7502. (e) Lithiation of Fluoroanisoles: Furlano, C. D.; Calderon, N. S.; Chen, G.; Kirk, L. K. *J. Org. Chem.* 1988, 53, 3145-1347. Ladd, L. D.; Weinstock, J. *J. Org. Chem.* 1981, 46, 203-206.

(4) Furlano, C. D.; Kirk, L. K. *J. Org. Chem.* 1986, 51, 4073-4075.

While a number of embodiments of this invention have been represented, it is apparent that the basic construction can be altered to provide other embodiments that utilize the invention without departing from the spirit and scope of the invention. All such modifications and variations are intended to be included within the scope of the invention as defined in the appended claims rather than the specific embodiments that have been presented by way of example.

We claim:

1. A method for preparing compound (2) from compound (5) having the formula:

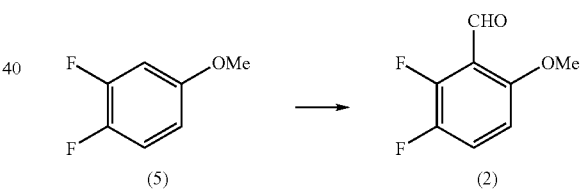

which comprises:
(a) admixing 3,4-difluoroanisole (5) with anhydrous magnesium chloride in an inert organic solvent;
(b) cooling the admixture from step (a) to about −78° C.;
(c) adding n-BuLi to the admixture in step (b) maintaining the temperature at about <−75° C.;
(d) adding N, N-dimethylformamide to the admixture in step (c) at about −78° C. maintaining the temperature at about <−75° C.;
(e) warming the admixture in step (d) to about 0° C. and then quenching the admixture with an aqueous acidic solution; and
(f) separating the organic solution from the aqueous solution in step (e) to provide compound (2) in the organic solution.

2. The method according to claim 1, wherein the inert organic solvent in step (a) is selected from the group consisting of 2-methyltetrahydrofuran, tetrahydrofuran, and diethyl ether.

3. The method according to claim 2, wherein the inert organic solvent is 2-methyltetrahydrofuran.

4. The method according to claim 1, wherein the molar ratio of (5) to magnesium chloride in step (a) is about 1:1.1, respectively.

5. The method according to claim 1, wherein the n-BuLi in step (c) is a 2.5M solution in hexanes.

6. The method according to claim 1, wherein the molar ratio of n-BuLi to (5) in step (c) is about 1.3:1, respectively.

7. The method according to claim 1, wherein the molar ratio of N,N-dimethylformamide to (5) in step (d) is about 1.4:1, respectively.

8. The method according to claim 1, wherein the aqueous acidic solution in step (e) is selected from the group consisting of citric acid solution, acetic acid, and formic acid.

9. The method according to claim 8, wherein the aqueous acidic solution is a citric acid solution.

10. A method for preparing compound (12) from compound (10) having the formula:

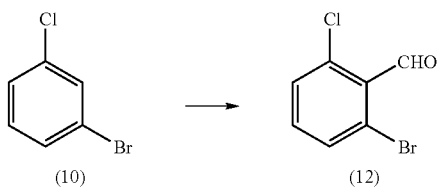

which comprises:
(a) admixing 3-bromochlorobenzene (10) with anhydrous magnesium chloride in an inert organic solvent;
(b) cooling the admixture from step (a) to about −78° C.;
(c) adding lithium diisopropylamide to the admixture in step (b) maintaining the temperature at about <−75° C.;
(d) adding N,N-dimethylformamide to the admixture in step (c) at about −78° C. maintaining the temperature at about <−75° C.;
(e) warming the admixture in step (d) to about 0° C. and then quenching the admixture with an aqueous acidic solution; and
(f) separating the organic solution from the aqueous solution in step (e) to provide compound (12) in the organic solution.

11. The method according to claim 10, wherein the inert organic solvent in step (a) is selected from the group consisting of 2-methyltetrahydrofuran, tetrahydrofuran, and diethyl ether.

12. The method according to claim 11, wherein the inert organic solvent is 2-methyltetrahydrofuran.

13. The method according to claim 10, wherein the molar ratio of (10) to magnesium chloride in step (a) is about 1:1.1, respectively.

14. The method according to claim 10, wherein the lithium diisopropylamide in step (c) is a 2M solution in heptane/tetrahydrofuran.

15. The method according to claim 10, wherein the molar ratio of lithium diisopropylamide to (10) in step (c) is about 1.3:1, respectively.

16. The method according to claim 10, wherein the molar ratio of N,N-dimethylformamide to (10) in step (d) is about 1.4:1, respectively.

17. The method according to claim 10, wherein the aqueous acidic solution in step (e) is selected from the group consisting of citric acid solution, acetic acid, and formic acid.

18. The method according to claim 17, wherein the aqueous acidic solution is a citric acid solution.

* * * * *